United States Patent [19]
Bowden et al.

[11] Patent Number: 5,369,494
[45] Date of Patent: Nov. 29, 1994

[54] PORTABLE SCANNING COLORIMETER

[75] Inventors: David R. Bowden; Timothy R. Friend, both of Grandville; Douglas V. Baker, Grand Rapids, all of Mich.

[73] Assignee: X-Rite, Incorporated, Grandville, Mich.

[21] Appl. No.: 45,859

[22] Filed: Apr. 12, 1993

[51] Int. Cl.$^5$ .................................................. G01J 3/51
[52] U.S. Cl. ..................................... 356/402; 356/405; 356/407
[58] Field of Search ............... 356/402, 404, 405, 406, 356/407, 425; 235/475, 482, 469, 379, 476; 382/7; 411/367

[56] References Cited

U.S. PATENT DOCUMENTS

| | | |
|---|---|---|
| 4,053,235 | 10/1977 | Hampton et al. . |
| 4,080,075 | 3/1978 | Berg . |
| 4,125,329 | 11/1978 | French et al. . |
| 4,402,611 | 9/1983 | Yuasa . |
| 4,505,589 | 3/1985 | Ott et al. . |
| 4,773,761 | 9/1988 | Sugiyama et al. . |
| 5,062,714 | 11/1991 | Peterson et al. ................ 356/406 |
| 5,073,028 | 12/1991 | Bowden et al. ................ 356/407 |
| 5,118,183 | 6/1992 | Cargill et al. . |
| 5,206,493 | 4/1993 | Anderson, Jr. et al. ......... 235/449 |

Primary Examiner—F. L. Evans
Assistant Examiner—Robert Kim
Attorney, Agent, or Firm—Varnum, Riddering, Schmidt & Howlett

[57] ABSTRACT

A portable colorimeter housing has an upper portion which is mounted on a lower portion in a cantilever fashion and is adapted to receive sheets larger than the device for purposes of obtaining tri-stimulus color measurements. An adjustable paper guide determines the distance that a sheet is inserted between upper and lower plates. A sheet to be measured inserted in the opening will operate a micro switch which activates a motor operative to advance the sheet between a motor-driven drive wheel in the lower plate and an idler roller in the upper plate. Transmittance or reflectance measurements are taken by means of photodetector cells including colorimetric filters. A user programmable processor performs pattern recognition and control functions. An optical housing assembly mounted on the upper plate includes a substantially cylindrical body provided with a horizontally extending channel and a mounting bar disposed in the channel is insulated from the cylindrical housing by air space except in peripheral areas of the cylindrical portion, thereby conducting heat generated by the high intensity light source to an area away from heat sensitive filters.

9 Claims, 10 Drawing Sheets

PORTABLE SCANNING COLORIMETER

BACKGROUND OF THE INVENTION

1. Field of the Invention

The invention relates to Color measuring apparatus and more particularly to colorimeters.

2. Background Art

Color measuring instruments for various applications are well known and described in various text books. A variety of different types of color measurements may be taken for different purposes. The measurement of color has had commercial application for many years. It is used, for example, to determine color consistency in photograph as well as the characteristics of color of printed materials, textiles, automobiles, etc. Different instruments are used for different purposes. The most comprehensive color measurements are obtained by instruments known as spectrophotometers which measure spectral distribution of light and give a percentage reflection or transmission at many points in the visible spectrum. These instruments are generally used for color appearance measurements. However, not all applications require the sophistication and accuracy of the spectrophotometer. Densitometers measure color density and are typically used for measuring specific materials such as printing inks and photographic dyes. Where specific color information is desired without the need for the sophistication of a spectrophotometer, a colorimeter may be used. The colorimeter is a tri-stimulant instrument which measures reflectance or transmittance through color filters which are properly related to properties of the human eye. The colorimeter is useful in photographic and color printing and reproduction applications as well as other applications.

The field of desk top publishing has expanded greatly in recent years and color printers have become ubiquitous. Color printers are often controlled by a program controlled processor which transmits control signals to the printer defining color to be produced. To assure color quality, it is desirable to be able to calibrate color printers to produce a selected quality of color for printed material produced by a number of different printers. Additionally, with increased data communication, data defining a color product may be transmitted to remote locations to be printed by a variety of printers. In order to be able to provide a product of consistent color characteristics, a comparison to a color standard is required. It is, therefore, desirable to provide a portable and inexpensive colorimeter which can be used to compare color characteristics of printed materials at various locations. Furthermore, it is desirable to provide an automatic scanning apparatus which can automatically scan color bars typically printed along an edge of color printed sheets.

SUMMARY OF THE INVENTION

In accordance with this invention, a portable colorimeter is provided which is inexpensive to manufacture. The portable colorimeter comprises a housing having a lower portion and an upper portion rigidly connected thereto in a cantilever fashion to allow an object sample such as a printed sheet to be inserted between the upper and lower portions for the purposes of obtaining tristimulus color measurements. Printed sheets typically will have an edge area with sample printed color blocks for test purposes. The edge area of the sheets may be inserted in the portable unit. A motor-driven drive wheel will advance the sheets through the unit at a preset speed, while a high intensity light is projected unto the sheet to be tested. Light transmitted or reflected by the object sample is projected through preselected filters onto photodetectors. A microprocessor, internal to the portable unit, is connected to the photodetectors and interprets the outputs of the photodetectors to compute color values which are stored or displayed on a display screen incorporated in the portable device.

In order to obtain accurate readings, the distances between the sample under test and the optical unit incorporating the detectors must be held within close tolerances. In the portable colorimeter of this invention, an opening is provided between a lower plate and a cantilevered upper plate to accommodate sheets of various widths.

An optical housing assembly incorporating a calibrated light source and photodetectors is supported on the upper plate. Because the angle at which reflected light is detected is critical, the cantilevered upper plate is connected at one end to the lower plate by means of screw fasteners and precision length spacers. Advantageously, this arrangement provides proper spacing and rigidity for the upper plate. The upper plate is preferable constructed of a light weight metal and lower plate may be fabricated of a thermoplastic material in order to provide a lightweight unit. Metallic angle brackets are added on the lower thermoplastic plate to provide a more rigid metal-to-metal connected structure with precise spacing.

An adjustable paper guide is provided which allows sheets with color bars at different distances from a side edge or with multiple color bars to be accommodated by the portable unit. The paper guide is provided with a ratchet mechanism which has a greater resistance in the direction of the force applied by a sheet, when it is inserted, than in the other direction. Advantageously, the ratchet mechanism engages an inner surface of downwardly extending edge lip so that the ratchet mechanism is covered from view.

The paper guide has an arm member which is provided with ribs extending above and below the main part of the arm member and into grooves in both the upper and lower plates to prevent sheets under test from slipping past the adjustment lever. Additionally, the grooves in the upper end lower plates are provided with sloping edges in the direction in which the sheet is advanced through the unit in order to prevent the sheet from being caught on an edge of one of the grooves.

The portable unit of this invention is provided with a novel optical housing particularly adapted to dissipate heat resulting from the high intensity lamp. The optical housing is a metallic housing having, near its periphery, a plurality of openings to accommodate the photodetectors and filters and has a separate metallic central portion with a central opening into which the high intensity lamp extends. Heat generated by a high intensity lamp is conducted away from the lamp by means of the separate central portion and heat is conducted away from the heat sensitive filters.

An object sample to be measured is advanced through the apparatus of this invention between a motor-driven drive wheel disposed in an aperture in the lower plate and an idler roller disposed in an aperture in the upper plate. A pair of support brackets, each having an opening adjacent one end supporting the idler roller, are mounted on the upper plate such that an opposite end of each bracket is supported on a shoulder area fashioned in the upper plate. In this manner, a substantially rigid support for the idler roller is provided.

In accordance with one aspect of the invention, a program controlled processor in the portable unit is programmable by the user. The processor is programmed to receive program information, temporarily store the information in a data memory, and subsequently execute a program from the data memory which stores updated program information in the program store. Advantageously, the arrangement, in accordance with this invention, avoids the necessity of returning a device to the manufacturer for each desired program revision.

BRIEF DESCRIPTION OF THE DRAWING

An illustrative embodiment of the invention is described below with respect to drawing, in which.

DETAILED DESCRIPTION

Figure 1:
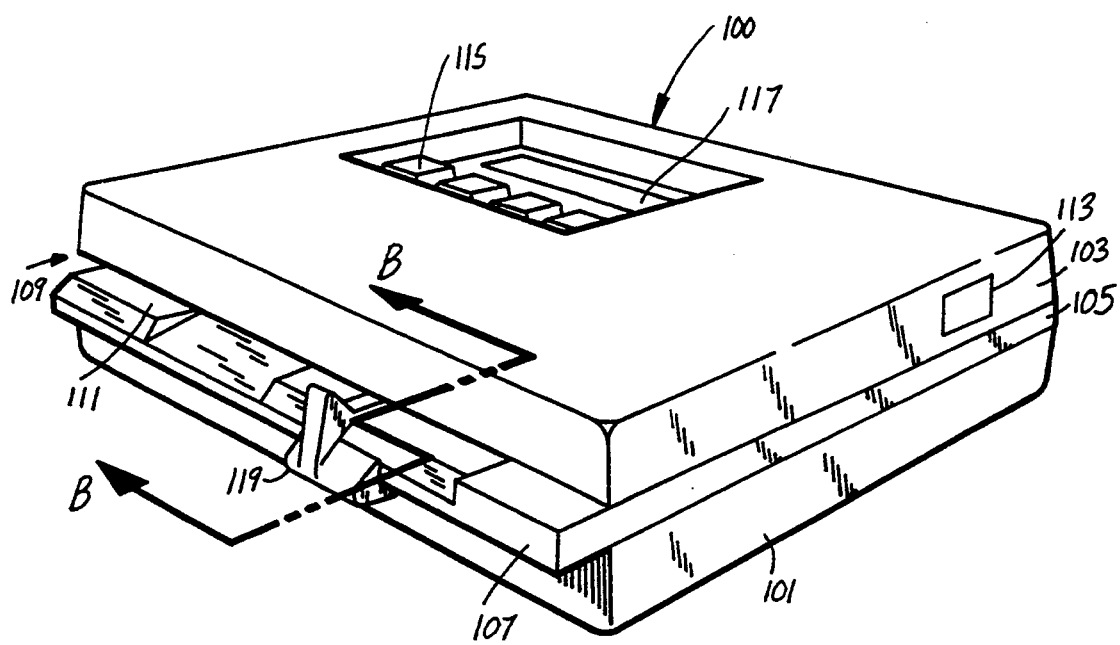
FIG. 1 is a perspective view of portable color measuring apparatus incorporating the principles of the invention.

FIG. 1 is a perspective view of portable color measuring apparatus 100 incorporating the principles of the invention. The apparatus has a lower housing 101, an upper housing 103 and a center housing assembly 105. The center housing assembly 105 includes a lower plate mounted on the lower housing having a substantial flat portion and a raised section 107 at one end. An upper plate, attached to the housing 103, is mounted on the lower plate in the area of the raised section 107 forming a spacial area 109 between the upper housing assembly 103 and upper surface 111 of the center housing assembly 105.

Figure 2:
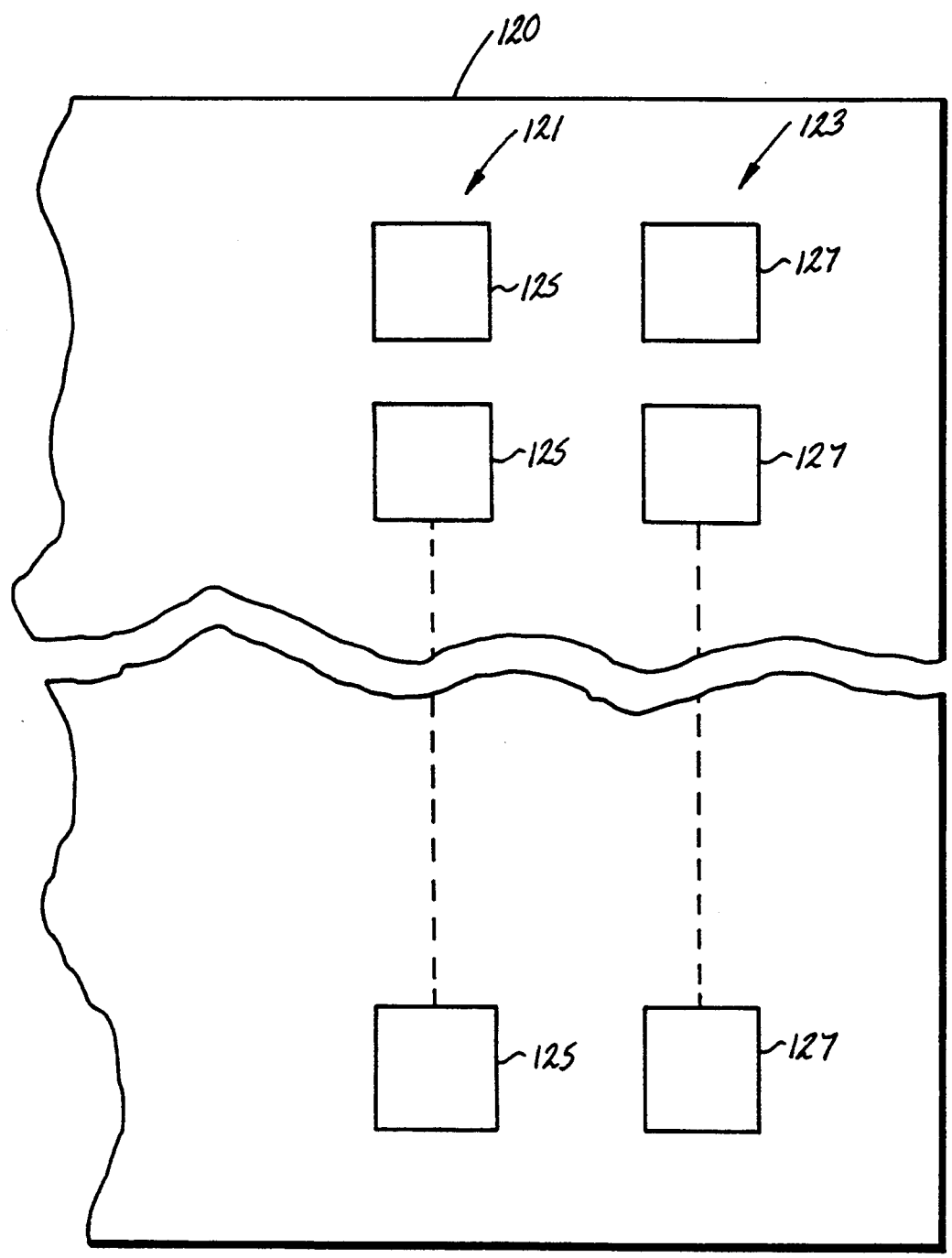
FIG. 2 is a representation of a sheet provided with color patches which may be inserted in the unit of FIG. 1.
Figure 3:
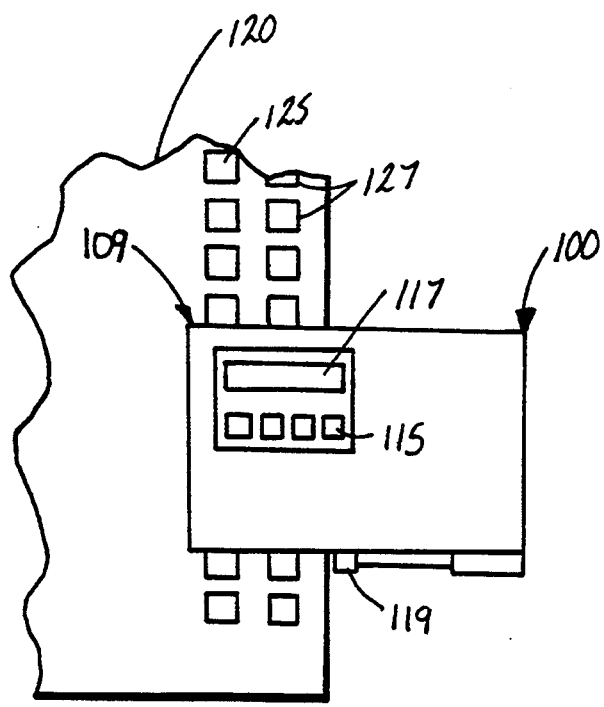
FIG. 3 is a diagrammatic representation of the sheet of FIG. 2 inserted in the apparatus of FIG. 1.

The apparatus 100 is particularly useful in desk top publishing applications in which a color printer connected to a computer prints in a variety of colors in accordance with specific control signals received from the computer. The same data defining the colors to be printed may be transmitted from one computer to a remotely located computer. Color printers are commercially available devices and, typically include color calibration. To assure that the color of products produced by the different printers are appropriately matched, the printers can be controlled to produce a color bar or several color bars such as color bars 121 and 123 sheet 120 represented in FIG. 2. Each of the color bars may include a number of color patches 125, 127 depicted in FIG. 2. Several hundred of such patches may be provided on a single sheet. Typically, each patch is lighter or darker than an adjacent patch, allowing a large number of readings to be obtained for each color. The color patches may be read by the colorimeter apparatus 100 by inserting the sheet in the opening 109, as depicted in FIG. 3. An electric motor internal to the unit 100 advances the sheet through opening 109 at a predetermined speed. Color measuring optics and associated electronic circuitry generate colorimeter data which may be stored in the apparatus 100 or transmitted to associated host computer equipment (not shown in the drawing) for further analysis. An RS232 input/output port 113 is provided for communications with the associated computer equipment. A set of input keys 115 may be used to enter certain data in the apparatus 100 and selected output information may be displayed on a liquid crystal display, or the like, 117. Apparatus 100 is a compact stand-alone unit and is adapted to store the data of multiple readings made by the device. The stored data is subsequently transferred via the input/output port 113 to a host computer for further analysis of the data, in a known fashion.

The sheet 120 may have a plurality of spaced-apart color bars 121, 123, of color patches 125, 127. A paper guide 119 is provided which may be selectively positioned in the opening 109 to guide the sheet 120 in a proper position for the reading of the color patches 125, 127 by optical devices internal to the colorimeter apparatus 100.

Figure 4:
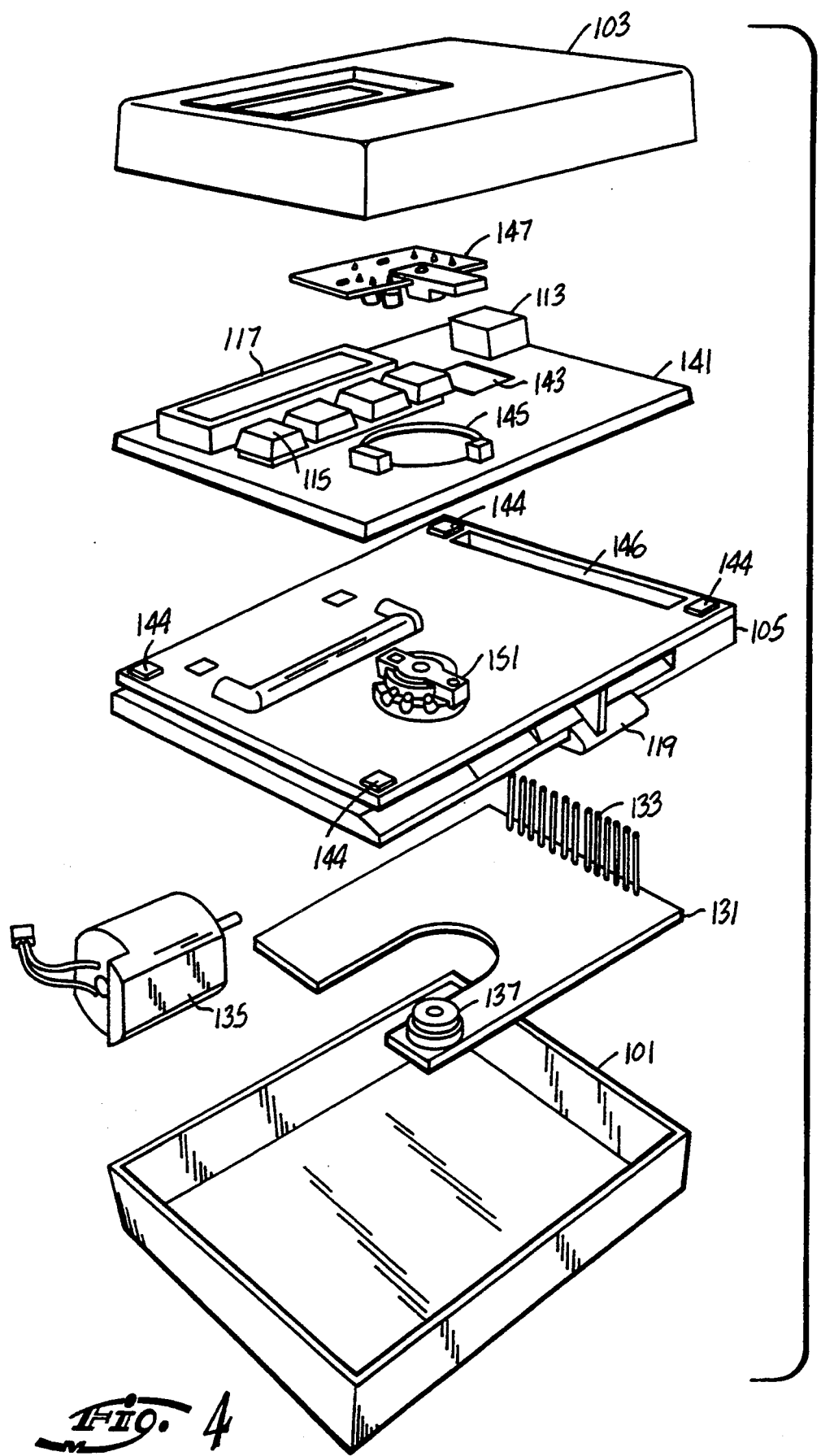
FIG. 4 is a an exploded view of the apparatus of FIG. 1.

FIG. 4 is an exploded view of the colorimeter apparatus 100. FIG. 4 shows the lower housing 101, which may contain a battery unit (not shown in the drawing) to provide electrical power to the colorimeter for stand-alone operation. A printed circuit board 131 is mounted on the lower housing and provides for electrical connections, via certain of the pins 133, to electric motor 135. The circuit board 131 supports the optical unit 137 used in certain applications to measure transmittances of an object sample under test. An upper circuit board 141 supports the key unit 115 and the display unit 117 as well as a processor 143. The circuit board 141 is mounted on the center housing assembly 105 on conductive pads 144 and is provided with an opening 145 to accommodate optical unit housing assembly 151. Optical unit circuit board 147 is mounted on the optical unit housing assembly 151 and supports a high intensity lamp and photo detectors (not shown in FIG. 4) used in making optical measurements from light reflected from an object sample. The upper circuit board 141 further supports the input/output connector 113.

The connector 113 is preferably a shielded connector to protect against EMI and RFI radiation. The upper circuit board 141 is provided with a further connector (not shown in the drawing) which engages pins 133 of circuit board 131. This connector and pins 133 extends through a slotted opening 146 in the center housing assembly 105. An upper housing 103 extends over circuit board 141 and attaches to the center housing assembly 105. The upper housing 103 and the lower housing 101 cover 130 are preferably made of lightweight plastic and covered with a copper reflective coating to shield the circuitry on the boards 131, 141 and 147 from EMI and RFI radiation.

Figure 5:
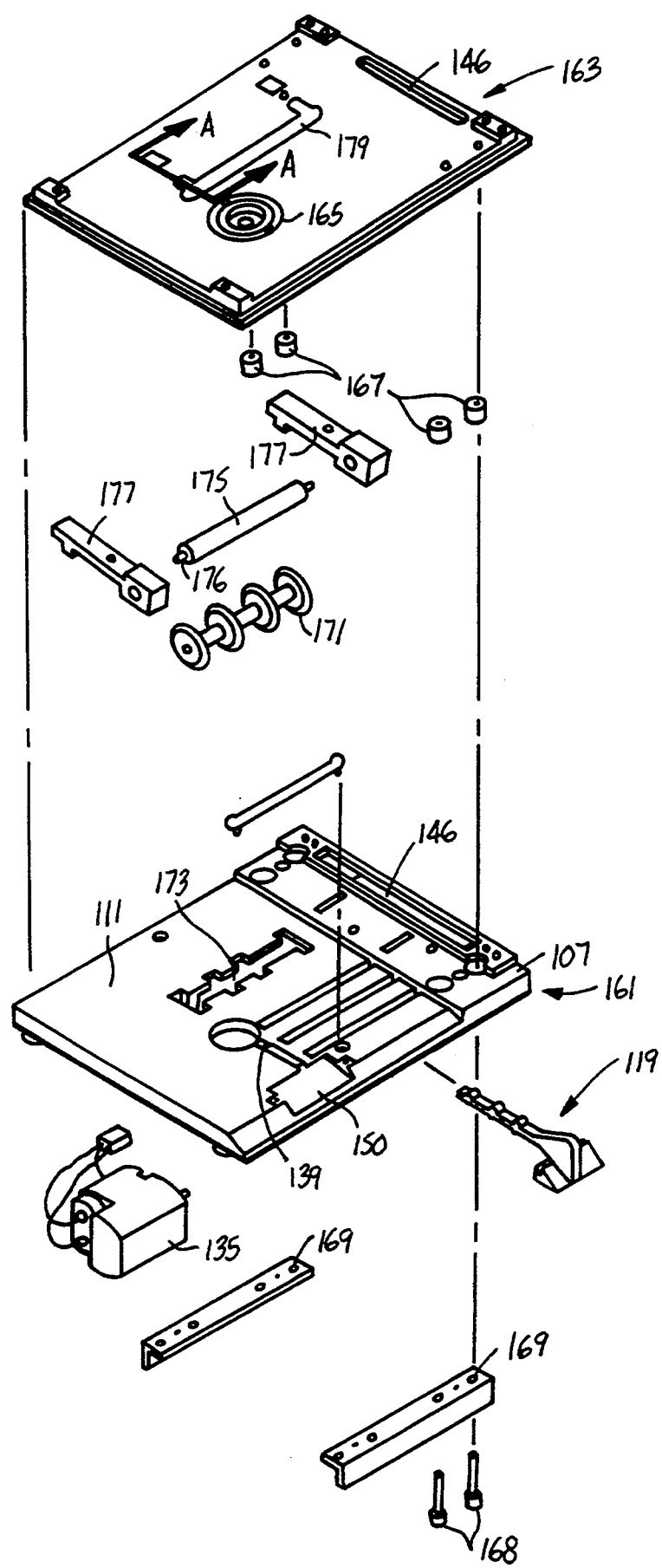
FIG. 5 is a exploded view of a center housing assembly of the apparatus of FIG. 1.

FIG. 5 is an exploded view of the center housing assembly 105 which includes a lower plate 161 which includes the raised section 107 and the upper surface 111 as shown in FIG. 1. An upper plate 163 is mounted on the lower plate 161 in the area of the raised section 107. Upper plate 163 is a metallic, preferably aluminum plate supporting the optical unit housing 151 which may be attached to the upper unit 163 in the area of the opening 165 by means of metallic screws or the like. A sheet of paper, such as the sheet 120, shown in FIG. 2, may be advanced between the upper plate 163 and the lower plate 161 and reflective optical measurements are taken by means a light projected from a light source in the optical housing 151 and reflected to photodetectors in the housing 151. The lower plate 161 may be constructed of a thermoplastic material such as the LEXAN BE2130 polycarbonate. The spacing between the paper and the optical housing 151 is critical for accurate readings. Therefore, structural rigidity of the cantilevered upper plate 163 is required. To assure proper spacing between the lower plate 161 and the upper plate 163, precision length metallic spacers 167 are provided. The metallic spacers, which may be machined to precision length, extend through the lower plate 161 and engage metallic brackets 169 which are attached to the lower side of the polycarbonate lower plate 161. This provides metal-to-metal contact through the polycarbonate lower plate 161. Two spacers 167 are preferably used on each of the two sides of the center housing assembly and are laterally spaced apart to lend rigidity to the cantilevered upper plate 163 to maintain proper separation between the upper and lower plates 163, 161 in the area of the optical housing 151.

The lower plate 161 is provided with a recessed portion 150 which can include appropriate graphical or numerical indices for purposes of indicating the center of the path for color measurements of narrow control strips or film strips. The lower plate 161 is further provided with a microswitch 139 which is enabled when a sheet or film strip is inserted in the opening 109 between the upper and lower plates 163, 161, to activate the motor 135.

Figure 6:
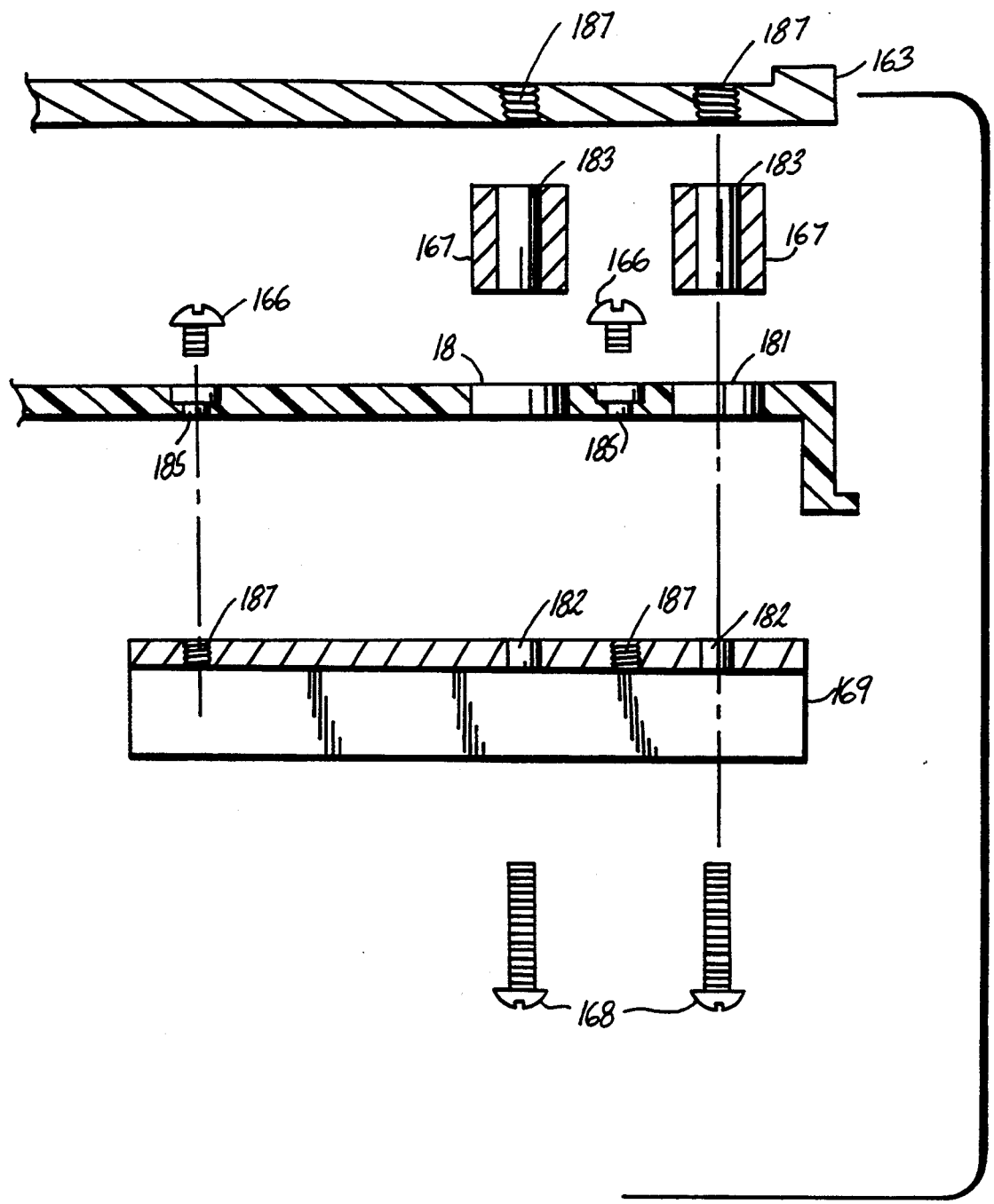
FIG. 6 is an enlarged cross-sectional exploded view of a structural interconnection arrangement of the assembly shown in FIG. 5.

FIG. 6 is a partial, cross-sectional exploded view of the upper and lower plates 163, 161, one of the brackets 169 and one pair of the precision length spacers 167. When assembled, the spacers 167 extend through openings 181 in bottom plate 161, having one and engaging the lower surface of upper plate 163 and another end engaging the upper surface of the bracket 169. A pair of screw-type fasteners 168 extend through openings 182 in the brackets 169 and openings 183 in the spacers 167 into threaded openings 184 in the upper plate 163. Another pair of screw-types fasteners 166 extend through counter sink openings 185 into threaded openings 187 of bracket 169. In this manner, a metal to metal connection of a precise distance defined by the spacers 167 provides rigidity of the upper plate and maintains proper separation. The rigidity is desirable for alignment and spacing of the optical housing 151 relative to an object sample advanced through the unit and for proper movement of the paper guide 119.

Proper spacing between the upper and lower plates 163, 161 is also important for proper tracking of sheets advanced through the spatial area by operation of motor 135, as described further below with reference to FIGS. 5 and 7. Referring again to FIG. 5, an object sample such as sheet 120 is advanced through the colorimeter apparatus 100 by means of electric motor 135 which may be conveniently mounted to the underside of the lower plate 161. Motor 135 drives a drive wheel assembly 171 which is supported in an aperture 173. An idler wheel assembly 175 is supported by means of support brackets 177 mounted on the underside of the upper plate 163. The idler wheel assembly 175 is partially received in an elongated aperture 179. When an object sample such as sheet 120 (FIG. 2) is inserted in the opening 109, defined between the upper and lower plates 163, 161, the underside of the sheet engaged by the drive wheel assembly 171 and the upper side of the sheet is engaged by the idler wheel assembly 175 to advance the sheet through the colorimeter apparatus 100 in direction parallel to the one end of the center housing assembly 105 where the upper and lower plates 161, 163 are interconnected and at a predetermined speed defined by the speed of the motor 135.

Figure 7:
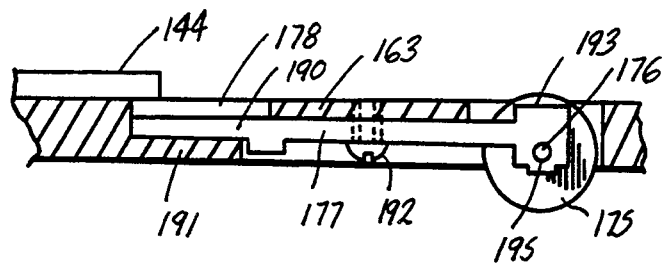
FIG. 7 is an enlarged cross-sectional view of a mounting arrangement for an idler roller support bracket.

FIG. 7 is a partial, enlarged cross-sectional view of a portion of the upper plate 163 along a line A—A in FIG. 5, showing the bracket 177 and idler roller 175 in position in the upper plate 163. The upper plate 163 is provided with an aperture 178 and a shoulder area 191. The bracket 177 is provided with an end piece 190 which engages the shoulder area 191 when the bracket is installed in the upper plate 163. The bracket 177 is fastened to upper plate 163 by means of a screw-type fastener 192. The upper plate 163 is provided with a further opening 179 which partially receives the idler roller 175. The bracket 177 has an enlarged section 193 provided with a bore 195 into which the shaft 176 of idler roller 175 is supported. The brackets 177 are preferably fabricated of a plastic material. When the colorimeter apparatus 100 is fully assembled and sheet, such a sheet 120, is advanced through the apparatus, an upwardly extending force is exerted against the roller 175 and the end of the bracket 177 in which the roller shaft is supported. This force is counter acted in part by the shoulder section 191 acting against the end section 190 of the bracket 177 such that only minor forces are exerted on the fastener 192. For proper tracking of the sheet as it advanced through 109, the tolerances of brackets 177, drive wheel assembly 171, and idler roller 175 must be properly controlled and the spacing between the upper and lower plates properly maintained. Furthermore, it is desirable to limit warping in the manufacturing process of the upper and lower plates to assure proper spacing.

Figure 8:
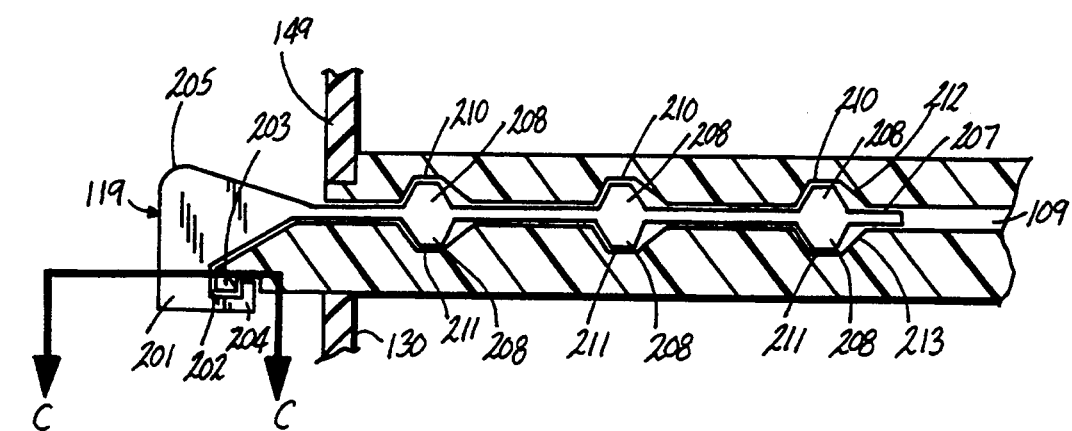
FIG. 8 is an enlarged cross-sectional view of the paper guide of FIG. 1 disposed between upper and lower plates of the center housing assembly.

FIG. 8 is a partial, enlarged cross-sectional view along line B—B of FIG. 1, showing the paper guide 119. The paper guide 119 is provided with a base section 201 having a channel area 202 which slidably engages a downwardly extending section 203 of the lower plate 161. An upwardly extending section 204 of the base area 201 engages one surface of the downwardly extending section 203 by a ratchet mechanism not visible in FIG. 8 and which is described later herein with reference to FIG. 9. The paper guide 119 is provided with a wing-like finger grip structure 205 to facilitate moving the paper guide between desired positions. Paper guide 119 is further provided with an arm member 207 extending between the upper plate 163 and the lower plate 161 to provide a stop which limits the distance which a sheet, such as sheet 120 (FIG. 2), may be extended into the opening 109. The arm member is provided with a plurality of ribs 208 extending above and below the arm section 207 and disposed in grooves 210 in the upper plate 163 and grooves 211 in the lower plate 161. The ribs provide additional rigidity to the arm member 207 but are provided primarily to prevent paper from sliding above or below the arm member 207. The grooves 210, 211 are provided with sloping surfaces 212 and 213, respectively, sloping away the wing-like finger grip structure 205 and in the direction in which a sheet is advanced through the colorimeter apparatus 100. The sloping surfaces are provided to reduce the possibility that the leading edge of a sheet being advanced through the apparatus will catch on an edge of the groove.

Figure 9:
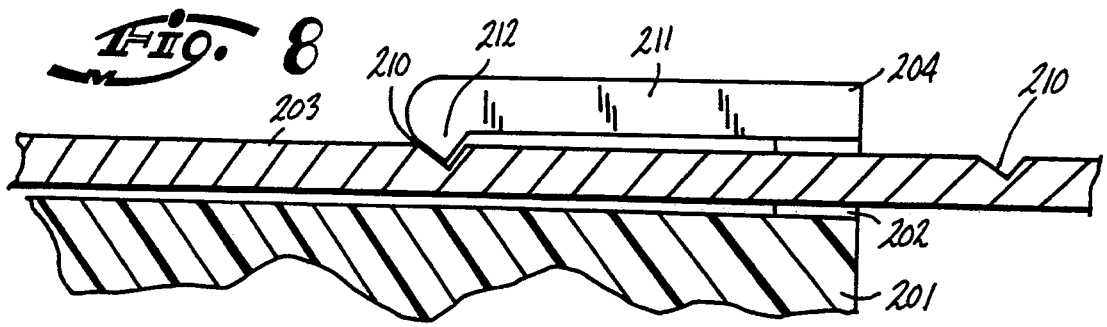
FIG. 9 is an enlarged, partial cross-sectional view of a ratchet mechanism for the paper guide of the apparatus of FIG. 1.

FIG. 9 is a partial, cross-sectional view along the line C—C of FIG. 8 showing a ratchet mechanism incorporated in the paper guide 119 and the downwardly extending section 203 of the lower plate 161. The section 203 is provided with grooves 210 and the upwardly extending section 204 of paper guide 119 is provided with a latching arm 211 having an end piece 212 which engages the grooves 210. The grooves 210 and the end piece 212 each have one sloped surface which is more nearly perpendicular to the outer side surface of the section 203 than the adjacent sloping surface. This arrangement provides for ease of movement in one direction, e.g., to the left in the configuration of FIG. 9, than in the opposite direction. This particular configuration is designed to provide greater resistance to sliding in the direction in which a sheet will be inserted in the opening 109. A plurality of grooves 210 are provided to accommodate reading of color strips in different areas of a sheet advanced through the colorimeter apparatus. The paper guide 119 is preferable made of a plastic material having sufficient resiliency in the arm 211 to allow for repeated disengagement and engagement of the arm 211 with the grooves 210.

Figure 10:
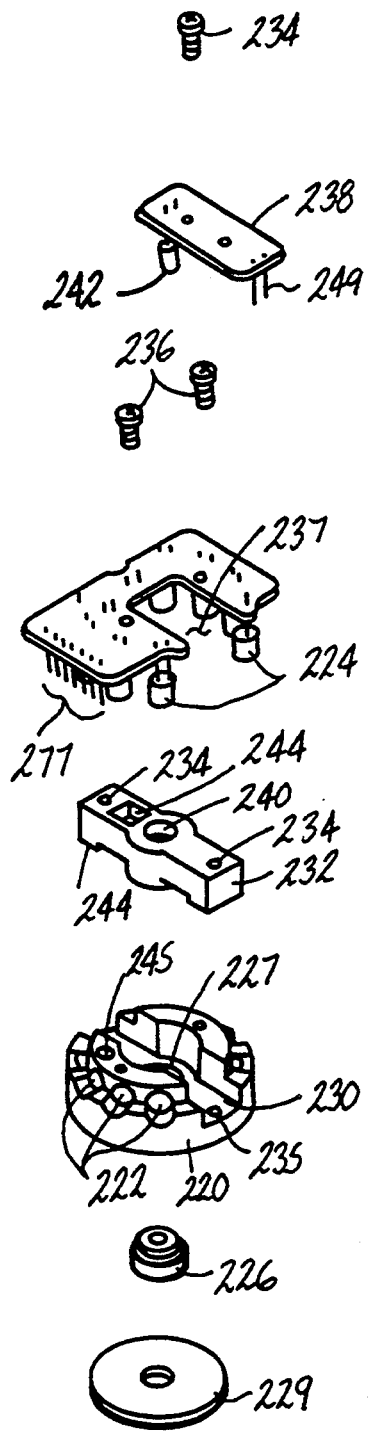
FIG. 10 is an exploded view of the optical housing and circuit board assembly of the apparatus of FIG. 1.

FIG. 10 is an exploded view of the optical unit housing assembly 151 and circuit board 147, shown in FIG. 4. The housing assembly 151 comprises a main housing body 220 provided with eight openings 222 around the periphery of the main housing body. These openings receive photoelectric cells 224 mounted on the main circuit board 225 of circuit board assembly 147. An aperture assembly 226 is mounted in a central bore 227 of the main housing 220, together with an infrared filter 229. The main housing 220 is mounted on the upper surface of the upper plate 163 and over the opening 165, shown in FIG. 5. The main housing 220 is provided with a cutaway channel 230 dimensioned to receive an elongated mounting bar 232. The main housing 220 is mounted to the upper plate 163 by means of screw-type fasteners extending through screw hole openings 234 in the mounting bar and screw hole openings 235 in the main housing 220 and extends into the upper plate 163.

Figure 11:
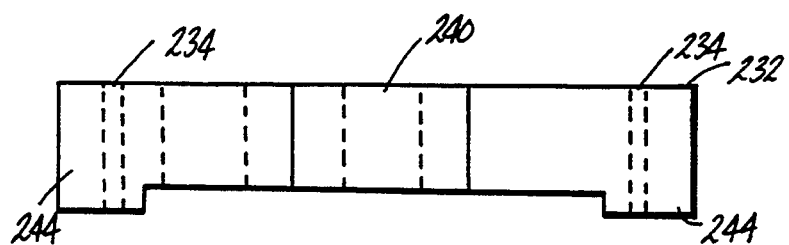
FIG. 11 is a side view of an optical housing mounting bar.

The circuit board 225 is attached to the main housing 220 by means of attachment screws 236 extending through the circuit board 225 and into the top surface of the main housing 220 while the cells 224 attached to the circuit board extend into corresponding openings 222 in the main housing. The circuit board 225 is provided with a rectangularly shaped opening 237. A lamp circuit board 238 is adapted to occupy the opening 237. The lamp circuit board 238 is attached by means of screw fasteners 239 to the mounting bar 232. The mounting bar 232 is provided with an enlarged center section and a central bore 240. The lamp 242 on circuit board 238 extends into the central bore 240 when the circuit board assembly 147 is attached to the main housing assembly 151. The lamp 242 is a high intensity lamp of the type typically used color measuring apparatus. Light from the lamp 242 is projected through the aperture assembly 226 and onto an object sample advanced through the colorimeter apparatus. Light reflected from the object sample is detected by the photoelectric cells 224 which are equipped with colorimetric filters with optical characteristics similar to the human eye. The characteristics of such filters are well known and described in available literature. The filters are heat sensitive and may be damaged in the presence of excessive heat. In colorimeter apparatus, the lamp 242 is operated continuously, as opposed to lamps in densitometers which are operated only on an intermittent basis. Consequently, substantially more heat is produced by the lamp in the colorimeter application. This heat, unless properly dissipated away form the photoelectric cells, which are of necessity in close proximation to the lamp, will cause damage to the filters and distort color measurement readings. The main housing 220 and the mounting bar 232 are constructed of a lightweight heat conductive metal such as aluminum. The mounting bar is provided as a separate piece which fits loosely in the channel 230 of the main housing in order to reduce the conduction of heat from the area of the central bore 240 in which the lamp 242 is contained, to the cells 224 mounted in the openings 222 of the main body. The mounting bar 232 is provided with pads 244, shown more clearly in the side view of FIG. 11. The mounting bar 232 is dimensioned such that the bar is insulated from the housing 220 by an envelope of air except in the area of the pads and the only contact between the bar and housing 220 is by means of the pads. Consequently, the heat generated in the mounting block 232 by lamp 242 is conducted to a peripheral area of the housing 220 away from cells 224 and is conducted into the metallic upper plate 163.

The mounting bar 232 is further provided with an aperture 244 which extends through the mounting bar and through a corresponding aperture (not visible in the drawing) in the main housing 220. The aperture 244 is provided to accommodate an a photoelectric detector mounted on the main circuit board 225 (not visible in the drawing) in addition to the cells 224. The additional detector is referred as a side sensor which senses the intensity of the light provided by the lamp 242. An additional aperture 245 in the main housing 220 is provided to accommodate a temperature sensor, also mounted on the main circuit board 225, which senses the temperature of the main housing. The circuit board 225 is connected via connector pins 247 to circuit board 141, shown in FIG. 4, and the lamp circuit board 238 is similarly connected via pins 249 to circuit board 141. The system's microprocessor on circuit board 141 is electrically connected to the circuit board 225 via circuit board 141. The microprocessor 143 processes electrical output signals received from the cells 224 representative of light reflected from an object sample and is responsive to the side sensor disposed in aperture 244 and the temperature sensor in aperture 245 to provide appropriate warning signals when certain preset limits are exceeded.

Figure 12:
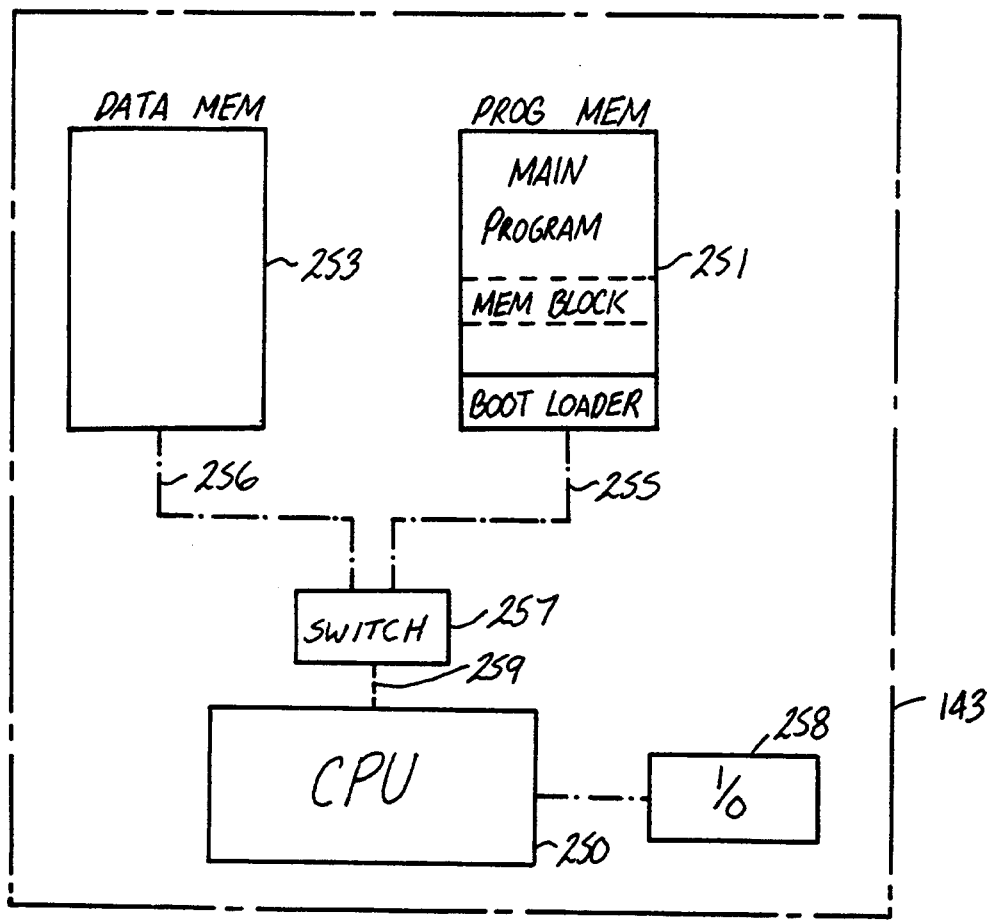
FIG. 12 is a block diagram representation of the program control processor internal to the apparatus of FIG. 1.

FIG. 12 is a block diagram representation of the processor 143 which is mounted on the circuit board 141 shown in FIG. 4. The processor 143 includes a center processing unit 250 as well as a program memory 251 and a random access data memory 252. The CPU 250 is connected to the memories 251 and 252 via memory buses 255 and 256, respectively, through a switch 257. The switch 257 is connected to the CPU via bus 259 which will include memory address and data bus leads for the memories 251, 252, as well as control leads for the switch 257. The switch 257 is a well known and commercially available device which is responsive to control signals from the CPU 250 to selectively connect certain portions of the bus 259 to memory buses 255 and 256. The CPU 250 is connected to an input/output interface 258 which may be connected to the input/output port 113, the keys 115 and the display 117, shown in FIG. 1, as well as photoelectric cells and sensors of circuit board 225, described with reference to FIG. 10. A primary function of the processor 143 is to execute pattern recognition programs stored in program memory 251 to distinguish color patterns of color strips advanced through the colorimeter apparatus. Basic methods for pattern recognition are known. One method is described is U.S. Pat. No. 5,062,714 dated Nov. 5, 1991 and issued to Peterson, et al, and that document is incorporated by reference herein. The function of the processor 143 is to recognize patterns of tri-stimulus values detected from the sensors 224 (FIG. 10) and to compare the detected patterns with patterns recorded in the program memory 251. The tri-stimulus values are typically designated as x, y, z and x'. Values for these designations are obtained from the cells 224. As mentioned earlier, eight such cells are mounted in the optical housing assembly 151 (FIG. 4). Two oppositely disposed cells are designated for each of the x, y, z and x' values and their output signals are additively combined. The x, y, z and x' characteristics of each of the cells are defined by filters interposed between the light reflected from the object sample and a photoelectric sensor, in a well known fashion.

In many color measurement systems such as densitometers used to determined color density consistency, the pattern recognition computations are compared with relatively fixed industry or system-wide standards. Such standards are incorporated in the color measuring apparatus, for example, in the form of pattern-defining data which is typically entered in the program memory at the time that the instrument is manufactured. However, in desk-top publishing or color copying and other applications, there tend to be no universal standards, and the standards may be defined by the user of the instrument. To that end, the instrument in accordance with the present invention has been provided with customer programmable capabilities as described below.

As shown in FIG. 12, the program memory 251 has a designated area for a main program which, when executed by the CPU 250 performs pattern recognition functions and other functions of the system. An area of the program memory 251 is dedicated to the storage of pattern recognition information, as mentioned earlier. Furthermore, a boot loader program is stored in the program memory 251 which is used to initialize the system when the apparatus is turned on. The program memory 250, as is typically the case, is a non-volatile memory which is not erased when power to the system is turned off. The program memory 251 is preferably a well-known and commercially available electrically erasable, programmable, read-only memory of a type known as a flash memory. The flash memory may be arranged to be electrically erasable under control of signals from the system's central processing unit such as CPU 250. Particularly, selected blocks of memory are typically erasable rather than individual memory locations. The data memory 252 may be a known random access memory which is typically erased when system power is turned off.

Figure 13:
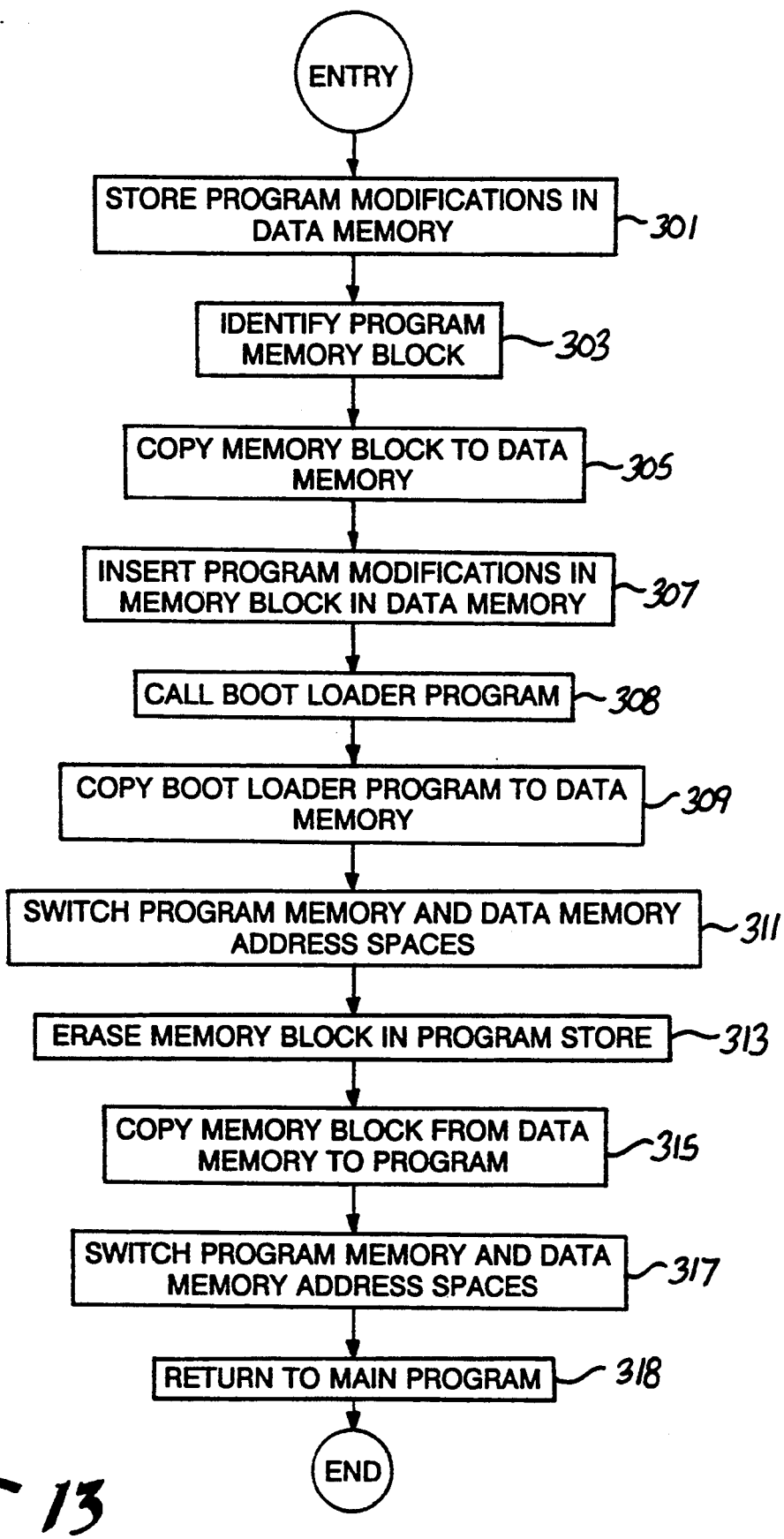
FIG. 13 is a flow diagram representation of a process for implementing customer programmability of the processor of the apparatus of FIG. 1.

FIG. 13 is a block diagram representation of a process executed in the processor 143 to provide programmability of the processor by the user of the product, without the necessity of returning the product to the manufacturer for a revision of the pattern recognition data or other criteria typically provided by the customer. FIG. 13 includes an entry point at which the program may be entered by the user by keying appropriate information in to the keys 115 or downloading data into the processor via the input/output port 113. Such data will be identified as program modifications in a specified area and are stored in a selected area of the data memory 252, as indicated in block 301 of FIG. 13. The next step in the process is to identify the program memory block in which the new information is to be entered, as indicated in block 303. The memory block may be defined as a block of the program memory which is erasable under control of the CPU 250. The size of the block will depend on the characteristics of the program memory. In the flash-type memories, the boundaries of erasable blocks are well defined. The next step is to copy the identified memory block in which modifications are to be made from the program memory 251 into a selected area of the data memory 252, as indicated in block 305 of FIG. 13. Thereafter, as indicated in block 307, the program modification data is inserted in the copied memory block in the data memory.

Subsequently, a call is made from the main program to the boot program, as indicated in block 308. The boot program copies relevant portions of itself from the program memory 251 to a selected area of the data memory 252 as represented by block 309 of FIG. 13. Thereafter, under control of the boot loader program, the program memory and data memory address spaces are switched, as indicated in block 311 of FIG. 13. This is accomplished by control signals from the CPU 250 to the switch 257 which reconfigure the switch 257 such that memory address control leads normally connected from bus 259 to program memory bus 255 are connected instead to data memory bus 256 (FIG. 12) and memory address control leads normally connected from bus 259 to data memory bus 256 are connected instead to the program memory bus 255. By means of appropriate control signals, the memory block of program memory 251 which has been transferred and stored in the data memory 252, as indicated in block 305 of FIG. 13, is erased in the program memory 251 under control of the boot loader program. This action is represented in block 313 of FIG. 13. Thereafter, as indicated in block 315, the memory block in which the program modifications have been inserted in block 307 is copied from the data memory 252 to the program memory 251 in the area of the program memory 251 which was erased in block 313, all under control of the boot loader program executed from the data memory 252. In this manner, the updated information supplied by the user has been entered in the program memory 251. By operation of the switch 257, under control of the boot loader program, the program memory and data memory address spaces are again switched. Thereafter, program memory addresses will again be directed to the program memory 251 and data memory addresses will be directed to the data memory 252. This step is represented in block 317 of FIG. 13. Finally, a return is made from the boot program to the main program, as indicated in BLOCK 318.

It will be understood that the above-described arrangement is merely illustrative of the application of the principals of the invention, and that other arrangements may be readily devised by those skilled in the art without departing from the spirit and scope of the invention.

We claim:

1. Portable colorimeter apparatus for measuring color characteristics of a sheet, the apparatus comprising:
   a generally rectangularly shaped housing assembly comprising spaced apart, upper and lower plates and having opposing sides and opposing ends;
   the upper plate having substantially flat upper and lower surfaces and an opening extending between the upper and lower surfaces;
   an optical unit mounted on the upper surface in alignment with the opening and comprising a plurality of color sensitive optical receivers;
   the lower plate comprising a substantially flat upper surface area and a drive wheel aperture;
   the upper and lower plates rigidly interconnected along only one end of the housing assembly with the upper plate extending over the lower plate in a cantilever fashion, forming a spatial area between the lower surface of the upper plate and the substantially flat upper surface area of the lower plate, the spatial area having openings on three sides of the housing assembly to receive a sheet to be measured having dimensions extending beyond the dimensions of the spatially area;
   a motor-driven drive wheel extending into the aperture and advancing the sheet in the spatial area in a direction of advancement generally parallel the one end;
   one of the upper and lower plates having a raised section extending in the spatial area along the one end and between the opposing sides and comprising a first pair of spaced apart aligned openings adjacent one of the sides and a second pair of spaced apart aligned openings adjacent the other of the sides;
   precision length spacers disposed in the pairs of aligned openings and fasteners extending between the upper and lower plates and through the spacers, whereby the fasteners and spacers ensure a proper distance relationship between the sheet and the optical unit while the sheet is advanced in the spatial area.

2. The apparatus in accordance with claim 1 wherein the upper plate is a metallic plate and the lower plate is constructed of a thermoplastic material provided with openings in alignment with the spacers and the spacers are metallic spacers machined to a specified length, the apparatus further comprising a pair of spaced apart, substantially parallel extending metallic brackets fastened to and disposed below the lower plate and wherein the spacers extend between the lower surface of the upper plate and through the openings in the lower plate to the metallic brackets.

3. The portable colorimeter apparatus in accordance with claim 1 and further comprising a paper guide disposed between the upper and lower plates and defining a limit of travel in a direction transverse to the direction of advancement of a sheet inserted in the opening, the paper guide comprising an arm member having substantially parallel upper and lower surfaces and extending in the direction of advancement between the upper and lower plates and transversely extending rib members on the upper and lower surfaces of the arm member, and wherein the lower surface of the upper plate and the upper surface area of the lower plates are provided with grooves extending in a direction transverse to the direction of advancement, and wherein the rib members are received in the grooves.

4. The apparatus in accordance with claim 3 wherein each of the grooves has at least one sidewall sloping in the direction of advancement.

5. The apparatus in accordance with claim 3 wherein the lower plate has a downwardly extending outer edge having a lower surface and an inner surface and spaced apart vertically extending grooves in the inner surface and the paper guide has a base section having a horizontally extending portion extending below the lower surface of the edge lip and an upwardly extending portion joined to the horizontally portion of the base section and comprising a ratchet arm having an end piece engaging different ones of the vertically extending grooves at selected different positions of the paper guide.

6. The apparatus in accordance with claim 5 wherein the end piece of the ratchet arm and each of the vertically extending grooves are shaped to provide greater resistance to movement in a direction toward the one end of the housing assembly than in the opposite direction, when the end piece is engaged in one of the vertically extending grooves.

7. The apparatus in accordance with claim 1 and further comprising an idler roller having opposite ends and a pair of support brackets, each having one end engaging one end of the roller and having opposite ends and wherein the upper plate has an aperture substantially in alignment with the aperture in the lower plate and wherein the idler roller is at least partially disposed in the aperture in the upper plate and wherein the upper plate further comprises a pair of spaced apart shoulder areas and the opposite end of each of the brackets engages one of the shoulder areas.

8. Portable colorimeter apparatus for measuring color characteristics of a sheet, the apparatus comprising:
   a generally rectangularly shaped housing assembly comprising spaced apart upper and lower plates;
   the upper plate having substantially flat upper and lower surfaces and an opening extending between the upper and lower surfaces;
   an optical unit mounted on the upper surface in alignment with the opening and comprising a plurality of photoelectric cells;
   the lower plate comprising a substantially flat upper surface area and a drive wheel aperture;
   the upper and lower plates rigidly interconnected along only one end of the housing assembly in a cantilever fashion, forming a spatial area between the lower surface of the upper plate and the substantially flat upper surface area of the lower plate, the spatial area having openings on three sides of the housing assembly to receive a sheet to be measured having dimensions extending beyond the dimensions of the spatially area; and
   a motor-driven drive wheel extending into the aperture and advancing the sheet in the spatial area in a direction of advancement generally parallel the one end;

the optical unit comprising a substantially cylindrically shaped housing having a plurality of spaced apart openings disposed along opposing peripheral sides and photodetector cells disposed in the openings and an elongated channel of substantially rectangular cross section extending along a horizontally centerline of the optical unit housing and having a bottom wall and opposing side walls;

the optical unit further comprising a mounting bar of generally rectangular cross section smaller than the rectangular cross section of the channel and disposed within the channel and spaced apart from the side walls of the channel, the mounting bar having a bottom wall extending substantially parallel the bottom wall of the channel and a top wall opposite the bottom wall of the mounting bar and an opening in the mounting bar extending from the top wall to the bottom wall of the mounting bar and a light source disposed in the opening in the mounting bar, the mounting bar comprising mounting pads along the bottom wall of the bar engaging the bottom wall of the channel adjacent opposing ends of the channel, whereby heat generated by the lamp is transferred through the mounting bar to opposing peripheral sides of the housing and away from the photodetector cells.

9. The apparatus in accordance with claim 8 wherein the upper plate is a metallic plate and the optical unit is forced against the upper plate by fasteners extending through the mounting bar and the optical unit housing and into the lower plate, thereby enhancing the transfer of heat from the bar and the optical unit housing to the upper plate.

* * * * *